United States Patent [19]
Leonard

[11] Patent Number: 5,912,173
[45] Date of Patent: Jun. 15, 1999

[54] TRANSGENIC MURINE MODEL FOR XSCID

[75] Inventor: Warren J. Leonard, Bethesda, Md.

[73] Assignee: The United States of America as represented by the Department of Health and Human Services, Washington, D.C.

[21] Appl. No.: 08/424,224

[22] Filed: Apr. 19, 1995

Related U.S. Application Data

[63] Continuation of application No. 08/121,435, Sep. 14, 1993, abandoned, which is a continuation-in-part of application No. 08/031,143, Mar. 12, 1993, Pat. No. 5,518,880.

[51] Int. Cl.$^6$ .............................. C12N 5/00; C12N 15/00; C07H 21/04; C07K 1/00
[52] U.S. Cl. ....................... 435/354; 435/320.1; 435/463; 435/465; 530/350; 536/23.5; 935/9; 935/22; 935/70
[58] Field of Search .............................. 435/172.3, 240.2, 435/320.1; 800/2, DIG. 1; 536/23.5; 935/70; 530/350

[56] References Cited

U.S. PATENT DOCUMENTS 5,106,728  4/1992  Conley et al. ................................ 435/6
5,434,340  7/1995  Krimpenfort et al. ........................ 800/2

OTHER PUBLICATIONS

KI Weinberg et al (1989) Pediatric Research 25(4/2):170A.
X Cao et al (1993) Proc Natl. Acad Sci USA:90:8464–8468.
N Kobayashi et al (1993) Gene 130:303–304.
MR Capecchi (1989) Science 244:1288–1292.
T. Takeshita et al (1992) Science 257:379–382.
TH Page et al (1991) Eur J Immunol 21:2133–2138.
S Kumaki et al (1993) Biochem Biophys Res Comm 193:356–363.
Gelfand, E.W. and Dosch, H.M. *Birth Defects: Original Article Series* 19 (3): 65–72 (1983).
Puck, J.M., et al. *J. Clin. Invest.* 79: 1395–1400 (1987).
Conley, M.E., et al. *Proc. Natl. Acad. Sci. USA* 85: 3090–3094 (1988).
Cooper, M.D. and Butler, J.L. *Fundamental Immunology*, (Paul, W.E. editor, Raven Press, New York), pp. 1034–1039 (1989).
Pahwa, R., et al. *Proc. Natl. Acad. Sci. USA* 86: 5069–5073 (1989).
Weinberg, M.D. and Parkman, R. *N. Engl. J. Med.* 322 (24): 1718–1723 (1990).
Chatila, T. et al. *Proc. Natl. Acad. Sci. USA* 87: 10033–10037 (1990).
Goodship, J., et al. *Clin. Exp. Immunol.* 83: 4–9 (1991).
Felsburg, P.J. and Somberg, R.L. *Immuno. Rev.* 3: 277–303 (1992).
Puck, J.M., et al. *Am. J. Hum. Genet.* 50: 742–748 (1992).
Hendriks, R.W., et al. *Clin. Genetics* 42(3): 114–121 (1992).
Conley, M.E. *Annu. Rev. Immunol.* 10: 215–238 (1992).
Takeshita, T., et al. *Intl. Immunology* 2(5): 477–480 (1990).
Sugamura, K., et al. *Lymph. Res.* 9(4): 539–542 (1990).
Asao, H., et al. *FEBS Letters* 304: 141–145 (1992).
Takeshita, T., et al. *Science* 257: 379–382 (1992).
Voss, S.D., et al. *J. Exp. Med.* 176: 531–541 (1992).
Zurawski, S.M. and Zurawski, G. *EMBO Journal* 11(11): 3905–3910 (1992).
Noguchi, M., et al. *The Journal of Biological Chemistry* 268: 13601–13608 (1993).
Noguchi, M., et al. *Cell* 73: 147–157 (1993).
K Theiler (1989) The House Mouse pp. 148–149.
K Ohbo et al (1996) Blood 87:956–967.
WJ Leonard et al (1995) Immunological Reviews 148:97–114.
A Gossler et al (1986) Proc Natl Acad Sci USA 83: 9065–9069.

*Primary Examiner*—Bruce R. Campbell
*Attorney, Agent, or Firm*—Venable; John W. Schneller

[57] ABSTRACT

The present invention provides an isolated nucleic acid sequence encoding murine IL-2Rγ. The present invention also provides a vector comprising a mutated IL-2Rγ nucleic acid which is capable of homologous recombination in at least some cells to which the vector is introduced. The present invention also provides an embryonic stem cell comprising a mutated IL-2Rγ nucleic acid integrated into the cell by homologous recombination following transfection with the vector above. The present invention further provides a blastocyst cell comprising the embryonic stem cell above. In addition, the present invention provides a transgenic animal comprising a mutated IL-2Rγ gene. In particular, the animal is a non-human mammal whose germ and somatic cells contain a mutated IL-2Rγ gene sequence introduced into said mammal, or an ancestor thereof, at an embryonic stage. The present invention also provides a method of producing a non-human mammal with XSCID which comprises introducing into at least some cells of the recipient animal a mutated IL-2Rγ gene. Lastly, the present invention provides a non-human animal produced by the method above, and progeny thereof, wherein at least some cells retain a mutated IL-2Rγ gene.

19 Claims, 1 Drawing Sheet

FIG. 1

```
CCCAGAGAAAGAAGAGCAAGCACCATGTTGAAACTATTATTGTCACCTAGATCCTTCTTAGTCCTTCAGCTGCTCCTGCTGAGGGCAGGG     90
                         MetLeuLysLeuLeuLeuSerProArgSerPheLeuValLeuGlnLeuLeuLeuLeuArgAlaGly
                          1                    10                   20

TGGAGCTCCAAGGTCCTCATGTCCAGTGCGAATGAAGACATCAAAGCTGATTTGATCCTGACTTCTACAGCCCCTGAACACCTCAGTGCT     180
TrpSerSerLysValLeuMetSerSerAlaAsnGluAspIleLysAlaAspLeuIleLeuThrSerThrAlaProGluHisLeuSerAla
                  30                   40                   50

CCCACTCTGCCCCTTCCAGAGGTTCAGTGCTTTGTGTTCAACATAGAGTACATGAATTGCACTTGGAATAGCAGTTCTGAGCCTCAGGCA     270
ProThrLeuProLeuProGluValGlnCysPheValPheAsnIleGluTyrMetAsnCysThrTrpAsnSerSerSerGluProGlnAla
                  60                   70                   80

ACCAACCTCACGCTGCACTATAGGTACAAGGTATCTGATAATAATACATTCCAGGAGTGCAGTCACTATTTGTTCTCCAAAGAGATTACT     360
ThrAsnLeuThrLeuHisTyrArgTyrLysValSerAspAsnAsnThrPheGlnGluCysSerHisTyrLeuPheSerLysGluIleThr
                  90                   100                  110

TCTGGCTGTCAGATACAAAAAGAAGATATCCAGCTCTACCAGACATTTGTTGTCCAGCTCCAGGACCCCCAGAAACCCCAGAGGCGAGCT     450
SerGlyCysGlnIleGlnLysGluAspIleGlnLeuTyrGlnThrPheValValGlnLeuGlnAspProGlnLysProGlnArgArgAla
                  120                  130                  140

GTACAGAAGCTAAACCTACAGAATCTTGTGATCCCACGGGCTCCAGAAAATCTAACACTCAGCAATCTGAGTGAATCCCAGCTAGAGCTG     540
ValGlnLysLeuAsnLeuGlnAsnLeuValIleProArgAlaProGluAsnLeuThrLeuSerAsnLeuSerGluSerGlnLeuGluLeu
                  150                  160                  170

AGATGGAAAAGCAGACATATTAAAGAACGCTGTTTACAATACTTGGTGCAGTACCGGAGCAACAGAGATCGAAGCTGGACGGAACTAATA     630
ArgTrpLysSerArgHisIleLysGluArgCysLeuGlnTyrLeuValGlnTyrArgSerAsnArgAspArgSerTrpThrGluLeuIle
                  180                  190                  200

GTGAATCATGAACCTAGATTCTCCCTGCCTAGTGTGGATGAGCTGAAACGGTACACATTTCGGGTTCGGAGCCGCTATAACCCAATCTGT     720
ValAsnHisGluProArgPheSerLeuProSerValAspGluLeuLysArgTyrThrPheArgValArgSerArgTyrAsnProIleCys
                  210                  220                  230

GGAAGTTCTCAACAGTGGAGTAAATGGAGCCAGCCTGTCCACTGGGGAGTCATACTGTAGAGGAGAATCCTTCCTTGTTTGCACTGGAA      810
GlySerSerGlnGlnTrpSerLysTrpSerGlnProValHisTrpGlySerHisThrValGluGluAsnProSerLeuPheAlaLeuGlu
                  240                  250                  260

GCTGTGCTTATCCCTGTTGGCACCATGGGGTTGATTATTACCCTGATCTTTGTGTACTGTTGGTTGGAACGAATGCCTCCAATTCCCCCC     900
AlaValLeuIleProValGlyThrMetGlyLeuIleIleThrLeuIlePheValTyrCysTrpLeuGluArgMetProProIlePro Pro
                  270                  280                  290

ATCAAGAATCTAGAGGATCTGGTTACTGAATACCAAGGGAACTTTTCGGCCTGGAGTGGTGTGTCTAAAGGGCTGACTGAGAGTCTGCAG     990
IleLysAsnLeuGluAspLeuValThrGluTyrGlnGlyAsnPheSerAlaTrpSerGlyValSerLysGlyLeuThrGluSerLeuGln
                  300                  310                  320

CCAGACTACAGTGAACGGTTCTGCCACGTCAGCGAGATTCCCCCCAAAGGAGGGGCCCTAGGAGAGGGGCCTGGAGGTTCTCCTTGCAGC     1080
ProAspTyrSerGluArgPheCysHisValSerGluIleProProLysGlyGlyAlaLeuGlyGluGlyProGlyGlySerProCysSer
                  330                  340                  350

CTGCATAGCCCTTACTGGCCTCCCCCATGTTATTCTCTGAAGCCGGAAGCCTGAACATCAATCCTTTGATGGAACCTCAAAGTCCTATAG     1170
LeuHisSerProTyrTrpProProProCysTyrSerLeuLysProGluAlaEnd
                  360         369

TCCTAAGTGACGCTAACCTCCCCTACTCACCTTGGCAATCTGGATCCAATGCTCACTGCCTTCCCTTGGGGCTAAGTTTCGATTTCCTGT     1260
CCCATGTAACTGCCTTTCTGTTCCATATGCCCTACTTGAGAGTGTCCCTTGCCCTCTTTCCCTGCACAAGCCCTCCCATGCCCAGCCTAA     1350
CACCTTTCCACTTTCTTTGAAGAGAGTCTTACCCTGTAGCCCAGGGTGGCTGGGAGCTCACTATGTAGCCAGGTTGGCCTCCAACTCACA     1440
GGCTATCCTCCCACCTCTCCCTCATAAGAGTTGGGGTTACTGGCATGCACCACCACACCCAGCATGGTCCTTCTCTTTTATAGGATTCTC     1530
CCTCCCTTTTTCTACCTATGATTCAACTGTTTCCAAATCAACAAGAAATAAAGTTTTTAACCAATGAAAAAAAAAAA               1608
```

TRANSGENIC MURINE MODEL FOR XSCID

This is a continuation of application Ser. No. 08/121,435, filed on Sep. 14, 1993, abandoned, which is a continuation-in-part application of U.S. Ser. No. 08/031,143, filed Mar. 12, 1993, the contents of which are hereby incorporated by reference.

BACKGROUND OF THE INVENTION

Severe combined immunodeficiency diseases (SCIDs) represent a spectrum of disorders characterized by profound defects of both cellular and humoral immunity (Cooper, M. D. and Butler, J. L. *Fundamental Immunology,* (Paul, W. E., editor, Raven Press, New York), pp. 1034–1039 (1989); Gelfand, E. W. and Dosch, H. M. *Birth Defects: Original Article Series* 19(3): 65–72 (1983); Conley, M. E. *Annu. Rev. Immunol.* 10: 215–238 (1992)). One in every $10^5$ to $10^6$ live births are affected by these diseases. Infants with SCID usually become ill in the first few months of life. While their growth and development may initially proceed normally, infections leading to cessation of growth soon become evident (Cooper, M. D. and Butler, J. L., supra, at 1034). Individuals with SCID are vulnerable to virtually every type of pathogenic microorganism, even those that rarely cause disease in normal individuals (Cooper, M. D. and Butler, J. L., supra, at 1034). Candida fungal infection of mucocutaneous surfaces is often the first indication of immunodeficiency, followed by intractable diarrhea and pneumonia (Cooper, M. D. and Butler, J. L., supra, at 1034). The majority of infected infants die before their first birthday.

Classical SCID ("Swiss-type agammaglobulinemia") is characterized by the absence of both T and B cells, presumably related to a defect affecting the lymphocytic stem cell. Autosomal recessive forms of SCID result from deficiencies of adenosine deaminase (ADA) or purine nucleoside phosphorylase (PNP), the inability to express class II molecules of the major histocompability complex ("Bare Lymphocyte Syndrome"), or defective IL-2 production. Other autosomal recessive forms have no known defect (Cooper, M. D. and Butler, J. L., supra, at 1034–1037; Gelfand, E. W. and Dosch, H. M., supra, at 66–67; Conley, supra, at 215–238).

X-linked severe combined immunodeficiency (XSCID) accounts for approximately half of all cases of SCID. This form of SCID is inherited in an X-linked fashion. XSCID is characterized by an absence of T-cells and histologic evidence of hypoplastic and abnormal differentiation of the thymic epithelium. Levels of B-cells are normal or even elevated, and therefore patients are only mildly lymphopenic (Cooper, M. D. and Butler, J. L., supra, at 1037; Gelfand, E. W. and Dosch, H. M., supra, at 66–70; Conley, M. E., supra, at 226–227). Since the B-cells are not functional, these males are hypo- or agammaglobulinemic.

In U.S. Ser. No. 08/031,143, filed Mar. 12, 1993, U.S Pat. No. 5,518,880 and in Noguchi, M., et al. *Cell* 73: 147–157 (1993), it was determined that XSCID results from a defective or mutated IL-2Rγ gene.

Human IL-2Rα (Leonard, W. J., et al. *Nature (London)* 311: 625–631 (1984); Nikaido, T., et al. *Nature (London)* 311: 631–635 (1984)), IL-2Rβ (Hatakcyama, M., et al. *Science* 244: 551–556 (1989)), and IL-2Rγ (Takeshita, T., et al. *Science* 257: 379–382 (1992)) cDNAs have been isolated. Murine cDNAs, however, have only been isolated for IL-2Rα (Miller, J., et al. *J. Immunol.* 134: 4212–4217 (1985); Shimuzu, A., et al. *Nucleic Acids Res.* 13: 1505–1516 (1985)) and IL-2Rβ (Kono, T., et al. *Proc. Natl. Acad. Sci. USA* 87: 1806–1810 (1990)).

The present invention is based upon the isolation of murine IL-2Rγ cDNA, and its uses thereof. One important application of the murine IL-2Rγ cDNA is the preparation of an IL-2Rγ deficient mouse. The IL-2Rγ deficient mouse should serve as an excellent animal model for XSCID.

SUMMARY OF THE INVENTION

The present invention provides an isolated nucleic acid sequence encoding murine IL-2Rγ.

The present invention also provides a vector comprising a mutated IL-2Rγ nucleic acid which is capable of homologous recombination in at least some cells to which the vector is introduced.

The present invention also provides an embryonic stem cell comprising a mutated IL-2Rγ nucleic acid integrated into the cell by homologous recombination following transfection with the vector above.

The present invention further provides a blastocyst cell comprising the embryonic stem cell above.

In addition, the present invention provides a transgenic animal comprising a mutated IL-2Rγ gene. In particular, the animal is a non-human mammal whose germ and somatic cells contain a mutated IL-2Rγ gene sequence introduced into said mammal, or an ancestor thereof, at an embryonic stage.

The present invention also provides a method of producing a non-human mammal with XSCID which comprises introducing into at least some cells of the recipient animal a mutated IL-2Rγ gene.

Lastly, the present invention provides a nonhuman animal produced by the method above, and progeny thereof, wherein at least some cells retain a mutated IL-2Rγ gene.

BRIEF DESCRIPTION OF THE FIGURES

FIG. 1. DNA and deduced amino acid sequence for murine IL-2Rγ (SEQ. ID. NOS. 1 and 2) The putative signal peptide and transmembrane domain are in italics; the transmembrane domain is additionally underscored with a heavy bar. The four conserved cysteines and the WSXWS motif are boxed. The ATG start codon, TGA stop codon, and AATAAA polyadenylylation signal are underlined. Each N-linked glycosylation consensus motif (Asn-X-Ser/Thr) is double underlined.

DETAILED DESCRIPTION OF THE INVENTION

The present invention provides an isolated nucleic acid sequence encoding murine IL-2Rγ. In the preferred embodiment, the nucleic acid sequence is selected from the group consisting of: (a) The nucleic acid sequence contained in FIG. 1, or a complementary strand thereof; (b) DNA sequences which hybridize to the DNA sequence defined in (a); and (c) DNA sequences, but for the degeneracy of the genetic code, would hybridize to the DNA sequences defined in (a) or (b). The present invention also provides a murine IL-2Rγ protein encoded by the isolated nucleic acid sequence above. Preferably, the protein has the amino acid sequence contained in FIG. 1.

The cDNA encoding the murine IL-2Rγ was isolated and characterized from a library prepared from mRNA from Con A activated splenocytes from CBA/Ca mice. The full length murine IL-2Rγ cDNA is 1608 bp with an open reading frame that encodes 369 amino acids, identical in length to the open reading frame of the human IL-2Rγ cDNA. Murine and human IL-2Rγ have 69 and 70% identity at the nucleotide and amino acid levels, respectively. The murine IL-2Rγ chain retains the WSXWS motif and four cysteine residues characteristic of cytokine receptor superfamily members (Bazan, J. F. *Proc. Natl. Acad. Sci. USA* 87: 6934–6938 (1990)). Six N-linked glycosylation sites (asn-X-ser/thr) are found in the extracellular domain. Although the human IL-2Rγ cytoplasmic domain has a region of limited homology to the fourth or fifth Src homology region 2 (SH2) subdomains (Takeshita, et al., supra), this region is less well conserved in mouse (in particular, arg 289 and thr 292 in human IL-2Rγ are conserved in Lck, Hck, Lyn, and Blk, but not in murine IL-2Rγ). A "leucine zipper" like motif was noted to exist in the human IL-2Rγ sequence (formed by leucines at residues 165, 172, 179, and 186)(Takeshita, et al., supra), although no clear functional role for this was demonstrated. In the murine sequence, leucines 165 and 172 are conserved, leucine 179 is replaced by isoleucine and the final leucine is at position 187 instead of 186. The lack of rigorous conservation in the murine sequence of the limited SH2 subdomain homology and leucine zipper like regions lessens the probability that they play critical roles.

The murine IL-2Rγ CDNA is preferably used to prepare a transgenic mouse containing a mutated IL-2Rγ CDNA. This mouse would be beneficial for studying XSCID, which results from a defective or mutated IL-2Rγ gene (see U.S. Ser. No. 08/031,143, filed Mar. 12, 1993U.S. Pat. No. 5,518,880) where it was shown that three patients with XSCID had different point mutations resulting in premature stop codons at lys 97, arg 267, and ser 286, respectively, resulting in truncations of 251, 81, and 62 amino acids, respectively, and wherein it was taught that other types of point mutations, such as those which affect residues required for IL-2 binding, would also be expected to be found if DNA from enough XSCID patients were sequenced.

A transgenic mouse may be prepared by homologous recombination techniques (see *Current Protocols in Molecular Biology,* edited by F. M. Ausubel, et al., Supp. 23, §IV, pp. 9.15–9.17 (1993)). The vectors used for homologous recombination may be insertion constructs or replacement constructs.

The insertion construct contains a region of homology to the target gene cloned as a single continuous sequence and is linearized by cleavage of a unique restriction site within the region of homology. Homologous recombination introduces the insertion construct sequences into the homologous site of the target gene, interrupting normal target-gene structure by adding sequences. As a result, the normal gene can be regenerated from the mutated target gene by an intrachromosomal recombination event. (see *Current Protocols in Molecular Biology,* supra, p. 9.15.1).

The replacement construct is more commonly used. It contains two regions of homology to the target gene located on either side of a mutation, which is usually a positive selectable marker. Homologous recombination proceeds by a double cross-over event that replaces the target-gene sequences with the replacement-construct sequences. Because no duplication of sequences occurs, the normal gene cannot be regenerated. (see *Current Protocols in Molecular Biology,* supra, p. 9.15.1).

Homologous recombination may be used to inactivate a gene completely ("knock out") by creating a deletion in part of the gene or by deleting the entire gene. Usually, the construct contains a target gene with a portion replaced with a drug-resistant gene such as neomycin. (see *Current Protocols in Molecular Biology,* supra, p. 9.15.3).

Homologous recombination may also be used to introduce subtle mutations (e.g. single point mutations). One known method is called the "hit and run" method (Hasty, et al., *Nature* 350: 243–246 (1991)). In the Hasty, et al. method, an insertion vector is used to introduce a duplication containing a mutation into the target gene. One copy of the duplicated region is removed under gancyclovir selection. Fifty percent of the time it will be the normal half, leaving the mutation. (see *Current Protocols in Molecular Biology,* supra, p. 9.15.4).

In the preferred embodiment, the vector pPNT (Tybulewicz, et al., *Cell* 65: 1153–1163 (1991)) is used to make a targeting IL-2Rγ construct. pPNT is a "replacement" (as opposed to "insertion") vector in which two fragments for homologous recombination flank the neomycin resistance gene. Expression of the neomycin resistance gene is driven by the PGK promoter. The neomycin resistance gene allows for positive selection. Downstream of the second fragment cloning site is the HSV thymidine kinase gene, also driven by the PGK promoter, which allows for negative selection. The procedures using the pPNT vector are well known and are described in *Current Protocols in Molecular Biology,* supra, pp. 9.16.1–9.16.9.

As an example of the subject invention, two IL-2Rγ genomic fragments of the murine IL-2Rγ which do not contain repetitive sequences were cloned into pPNT. The plasmid was linearized with Not 1 and transfected into J1 embryonic stem cells (gift of R. Jaenisch, MIT) derived from 129 strain mice (i.e., the same strain as the genomic library in order to maximize the sequence identity for efficient homologous recombination).

G418 and gancyclovir were added 24 hours following transfection to effect "positive-negative selection" in which G418 is used to positively select colonies containing the neomycin resistance gene and gancyclovir is used to eliminate random integration. In random integration, the flanking TK gene is retained and confers gancyclovir sensitivity, whereas in homologous recombination the TK gene will be lost due to cross-over and the cells will be gancyclovir resistant. Gancyclovir selection also helps to eliminate multiple copies of the DNA fragments so that clones with single integrated fragments were obtained.

The clones are then analyzed for homologous recombination by Southern blot and/or PCR making use of sequences flanking the fragments used for homologous recombination to confirm that the site of integration is indeed at the IL-2Rγ locus rather than at a random locus.

The IL-2Rγ deficient ES cells are then infected into blastocysts and subsequently implanted into female mice by known procedures. It should be noted that J1 ES cells are of male lineage and therefore contain only a single X chromosome. As a result, only a single "knockout" is required to make an IL-2Rγ deficient ES cell. After IL-2Rγ deficient ES cells are injected into blastocysts, the initial mice obtained will be healthy chimeras. The germline will have both normal and mutated X chromosome bearing cells depending on whether they are derived from the normal blastocyst derived cells or the mutant ES cells. Breeding will yield heterozygous females who then have the possibility of having IL-2Rγ deficient male offspring. It is possible that these males will be severely immunodeficient. However, given the ability to breed the mice in microisolator sterile environments, they may be able to survive if shielded from infection.

Transgenic mice also may be prepared by using the technique of recombination activating gene (RAG)-2-deficient blastocyst complementation (Chen, et al., *Proc. Natl. Acad. Sci.* 90: 4228–4232 (1993)). The principle of this method is that RAG-2 deficient blastocysts generate chimeras with mature B and T cells which derive from the injected ES cells. This method offers the ability to create an IL-2Rγ deficient ES cell which can be complemented with IL-2Rγ constructs containing subtle mutations whose functional significance is to be evaluated. In this fashion, multiple different IL-2Rγ constructs may be injected into IL-2Rγ deficient ES cells and progeny mice studied far faster than multiple transgenic lines could be established for mating.

All publications mentioned hereinabove are hereby incorporated by reference in their entirety.

While the foregoing invention has been described in some detail for purposes of clarity and understanding, it will be appreciated by one skilled in the art from a reading of the disclosure that the invention should not be construed to be limited as such, and that various changes in form and detail can be made without departing from the true scope of the invention in the appended claims.

What is claimed is:

1. A vector for producing a mutated murine IL-2Rγ nucleic acid, the vector comprising an IL-2Rγ construct which is capable of homologous recombination with X-chromosomal DNA in murine cells into which the vector is introduced, thereby causing an IL-2Rγ deficiency.

2. A murine embryonic stem cell comprising a mutated IL-2Rγ nucleic acid in the X chromosome of the cell produced by homologous recombination following transfection with the vector of claim 1.

3. A vector of claim 1 wherein the mutated murine IL-2Rγ nucleic acid encodes an IL-2Rγ protein truncated by at least 62 C-terminal amino acids.

4. The vector of claim 3 wherein the mutated murine IL-2Rγ nucleic acid encodes an IL-2Rγ protein truncated by 251 C-terminal amino acids.

5. The vector of claim 3 wherein the mutated murine IL-2Rγ nucleic acid encodes an IL-2Rγ protein truncated by 81 C-terminal amino acids.

6. The vector of claim 3 wherein the mutated murine IL-2Rγ nucleic acid encodes an IL-2Rγ protein truncated by 62 C-terminal amino acids.

7. A method of producing a transfected mouse cell, comprising using the vector of claim 1 to provide a mutated IL-2Rγ gene in the X chromosome of a mouse cell, resulting in an IL-2Rγ deficiency.

8. A method according to claim 7, wherein the mouse cell is an embryonic stem cell.

9. A method comprising providing a vector comprising a mutated IL-2Rγ nucleic acid construct which is capable of homologous recombination with X chromosomal DNA in murine cells into which the vector is introduced, transfecting embryonic stem cells with the vector, selecting a transfected IL-2Rγ-deficient embryonic stem cell resulting from homologous recombination, injecting the transfected stem cell into a blastocyst, implanting the blastocyst in a female mouse, and obtaining progeny mice having an IL-2Rγ deficiency.

10. The method of claim 9, wherein the IL-2Rγ deficiency is an X-linked severe combined immunodeficiency disease.

11. The method of claim 9, further comprising injecting multiple different IL-2Rγ constructs into the IL-2Rγ deficient embryonic stem cell.

12. A vector comprising a mutated IL-2Rγ nucleic acid construct which is capable of homologous recombination with genomic DNA in murine cells into which the vector is introduced.

13. A vector according to claim 12, wherein the construct is an insertion construct.

14. A vector according to claim 12, wherein the construct is a replacement construct.

15. An IL-2Rγ deficient mouse cell host stably transfected with the vector of claim 12.

16. An isolated nucleic acid sequence encoding murine IL-2Rγ.

17. The nucleic acid sequence of claim 16 comprising the nucleic acid sequence of SEQ ID NO:1 or a complementary strand thereof.

18. A murine IL-2Rγ protein having the amino acid sequence of SEQ ID NO:2.

19. A transgenic mouse cell comprising a mutated IL-2Rγ gene construct having a sequence different from that of SEQ ID NO:1.

* * * * *

SEQUENCE LISTING (1) GENERAL INFORMATION:

(iii) NUMBER OF SEQUENCES:  2

(2) INFORMATION FOR SEQ ID NO:1:

(i) SEQUENCE CHARACTERISTICS:
      (A) LENGTH:  1608
      (B) TYPE:  NUCLEIC ACID
      (C) STRANDEDNESS:  SINGLE
      (D) TOPOLOGY:  UNKNOWN (ii) MOLECULE TYPE:
      (A) DESCRIPTION:  OLIGONUCLEOTIDE (iii) HYPOTHETICAL:  NO (iv) ANTI-SENSE:  NO (vi) ORIGINAL SOURCE:
      (A) ORGANISM:  MURINE
      (C) INDIVIDUAL ISOLATE:  IL-2R (xi) SEQUENCE DESCRIPTION:SEQ ID NO:1:

```
CCCAGAGAAA GAAGAGCAAG CACC ATG TTG AAA CTA TTA TTG TCA CCT          48
                           Met Leu Lys Leu Leu Leu Ser Pro
                           1               5

AGA TCC TTC TTA GTC CTT CAG CTG CTC CTG CTG AGG GCA GGG              90
Arg Ser Phe Leu Val Leu Gln Leu Leu Leu Leu Arg Ala Gly
        10              15                  20

TGG AGC TCC AAG GTC CTC ATG TCC AGT GCG AAT GAA GAC ATC             132
Trp Ser Ser Lys Val Leu Met Ser Ser Ala Asn Glu Asp Ile
            25                  30                  35

AAA GCT GAT TTG ATC CTG ACT TCT ACA GCC CCT GAA CAC CTC             174
Lys Ala Asp Leu Ile Leu Thr Ser Thr Ala Pro Glu His Leu
                40                  45                  50

AGT GCT CCC ACT CTG CCC CTT CCA GAG GTT CAG TGC TTT GTG             216
Ser Ala Pro Thr Leu Pro Leu Pro Glu Val Gln Cys Phe Val
                    55                  60

TTC AAC ATA GAG TAC ATG AAT TGC ACT TGG AAT AGC AGT TCT             258
Phe Asn Ile Glu Tyr Met Asn Cys Thr Trp Asn Ser Ser Ser
65                  70                  75

GAG CCT CAG GCA ACC AAC CTC ACG CTG CAC TAT AGG TAC AAG             300
Glu Pro Gln Ala Thr Asn Leu Thr Leu His Tyr Arg Tyr Lys
        80                  85                  90

GTA TCT GAT AAT AAT ACA TTC CAG GAG TGC AGT CAC TAT TTG             342
Val Ser Asp Asn Asn Thr Phe Gln Glu Cys Ser His Tyr Leu
            95                  100                 105

TTC TCC AAA GAG ATT ACT TCT GGC TGT CAG ATA CAA AAA GAA             384
Phe Ser Lys Glu Ile Thr Ser Gly Cys Gln Ile Gln Lys Glu
                110                 115                 120

GAT ATC CAG CTC TAC CAG ACA TTT GTT GTC CAG CTC CAG GAC             426
Asp Ile Gln Leu Tyr Gln Thr Phe Val Val Gln Leu Gln Asp
                    125                 130
```

-continued

| | |
|---|---|
| CCC CAG AAA CCC CAG AGG CGA GCT GTA CAG AAG CTA AAC CTA<br>Pro Gln Lys Pro Gln Arg Arg Ala Val Gln Lys Leu Asn Leu<br>135                  140                      145 | 468 |
| CAG AAT CTT GTG ATC CCA CGG GCT CCA GAA AAT CTA ACA CTC<br>Gln Asn Leu Val Ile Pro Arg Ala Pro Glu Asn Leu Thr Leu<br>     150                155                  160 | 510 |
| AGC AAT CTG AGT GAA TCC CAG CTA GAG CTG AGA TGG AAA AGC<br>Ser Asn Leu Ser Glu Ser Gln Leu Glu Leu Arg Trp Lys Ser<br>         165                170                  175 | 552 |
| AGA CAT ATT AAA GAA CGC TGT TTA CAA TAC TTG GTG CAG TAC<br>Arg His Ile Lys Glu Arg Cys Leu Gln Tyr Leu Val Gln Tyr<br>180                  185                      190 | 594 |
| CGG AGC AAC AGA GAT CGA AGC TGG ACG GAA CTA ATA GTG AAT<br>Arg Ser Asn Arg Asp Arg Ser Trp Thr Glu Leu Ile Val Asn<br>     195                200 | 636 |
| CAT GAA CCT AGA TTC TCC CTG CCT AGT GTG GAT GAC CTG AAA<br>His Glu Pro Arg Phe Ser Leu Pro Ser Val Asp Glu Leu Lys<br>205                  210                  215 | 678 |
| CGG TAC ACA TTT CGG GTT CGG AGC CGC TAT AAC CCA ATC TGT<br>Arg Tyr Thr Phe Arg Val Arg Ser Arg Tyr Asn Pro Ile Cys<br>220                  225                  230 | 720 |
| GGA AGT TCT CAA CAG TGG AGT AAA TGG AGC CAG CCT GTC CAC<br>Gly Ser Ser Gln Gln Trp Ser Lys Trp Ser Gln Pro Val His<br>         235                240                  245 | 762 |
| TGG GGG AGT CAT ACT GTA GAG GAG AAT CCT TCC TTG TTT GCA<br>Trp Gly Ser His Thr Val Glu Glu Asn Pro Ser Leu Phe Ala<br>              250                  255                  260 | 804 |
| CTG GAA GCT GTG CTT ATC CCT GTT GGC ACC ATG GGG TTG ATT<br>Leu Glu Ala Val Leu Ile Pro Val Gly Thr Met Gly Leu Ile<br>              265                  270 | 846 |
| ATT ACC CTG ATC TTT GTG TAC TGT TGG TTG GAA CGA ATG CCT<br>Ile Thr Leu Ile Phe Val Tyr Cys Trp Leu Glu Arg Met Pro<br>275                  280                  285 | 888 |
| CCA ATT CCC CCC ATC AAG AAT CTA GAG GAT CTG GTT ACT GAA<br>Pro Ile Pro Pro Ile Lys Asn Leu Glu Asp Leu Val Thr Glu<br>     290                295                  300 | 930 |
| TAC CAA GGG AAC TTT TCC GCC TGG AGT GGT GTG TCT AAA GGG<br>Tyr Gln Gly Asn Phe Ser Ala Trp Ser Gly Val Ser Lys Gly<br>         305                310                  315 | 972 |
| CTG ACT GAG AGT CTG CAG CCA GAC TAC AGT GAA CGG TTC TGC<br>Leu Thr Glu Ser Leu Gln Pro Asp Tyr Ser Glu Arg Phe Cys<br>              320                  325                  330 | 1014 |
| CAG GTC AGC GAG ATT CCC CCC AAA GGA GGG GCC CTA GGA GAG<br>His Val Ser Glu Ile Pro Pro Lys Gly Gly Ala Leu Gly Glu<br>              335                  340 | 1056 |
| GGG CCT GGA GGT TCT CCT TGC AGC CTG CAT AGC CCT TAC TGG<br>Gly Pro Gly Gly Ser Pro Cys Ser Leu His Ser Pro Tyr Trp<br>345                  350                  355 | 1098 |
| CCT CCC CCA TGT TAT TCT CTG AAG CCG GAA GCC TGAACATCAA<br>Pro Pro Pro Cys Tyr Ser Leu Lys Pro Glu Ala<br>     360                365 | 1141 |
| TCCTTTGATG GAACCTCAAA GTCCTATAGT CCTAAGTGAC GCTAACCTCC | 1191 |
| CCTACTCACC TTGGCAATCT GGATCCAATG CTCACTGCCT TCCCTTGGGG | 1241 |
| CTAAGTTTCG ATTTCCTGTC CCATGTAACT GCCTTTCTGT TCCATATGCC | 1291 |
| CTACTTGAGA GTGTCCCTTG CCCTCTTTCC CTGCACAAGC CCTCCCATGC | 1341 |
| CCAGCCTAAC ACCTTTCCAC TTTCTTTGAA GAGAGTCTTA CCCTGTAGCC | 1391 |
| CAGGGTGGCT GGGAGCTCAC TATGTAGCCA GGTTGGCCTC CAACTCACAG | 1441 |

```
GCTATCCTCC CACCTCTGCC TCATAAGAGT TGGGGTTACT GGCATGCACC              1491

ACCACACCCA GCATGGTCCT TCTCTTTTAT AGGATTCTCC CTCCCTTTTT              1541

CTACCTATGA TTCAACTGTT TCCAAATCAA CAAGAAATAA AGTTTTTAAC              1591

CAATGAAAAA AAAAAAA                                                  1608

(2) INFORMATION FOR SEQ ID NO:2:

(i) SEQUENCE CHARACTERISTICS:
        (A) LENGTH:  369
        (B) TYPE:  AMINO ACID
        (D) TOPOLOGY:  UNKNOWN (ii) MOLECULE TYPE:
        (A) DESCRIPTION:  PROTEIN (iii) HYPOTHETICAL:  NO (vi) ORIGINAL SOURCE:
        (A) ORGANISM:  MURINE
        (C) INDIVIDUAL ISOLATE:  IL-2R (xi) SEQUENCE DESCRIPTION:SEQ ID NO:2:

Met Leu Lys Leu Leu Ser Pro Arg Ser Phe Leu Val Leu Gln
 1               5                  10                  15

Leu Leu Leu Leu Arg Ala Gly Trp Ser Ser Lys Val Leu Met Ser
                20                  25                  30

Ser Ala Asn Glu Asp Ile Lys Ala Asp Leu Ile Leu Thr Ser Thr
                35                  40                  45

Ala Pro Glu His Leu Ser Ala Pro Thr Leu Pro Leu Pro Glu Val
                50                  55                  60

Gln Cys Phe Val Phe Asn Ile Glu Tyr Met Asn Cys Thr Trp Asn
                65                  70                  75

Ser Ser Ser Glu Pro Gln Ala Thr Asn Leu Thr Leu His Tyr Arg
                80                  85                  90

Tyr Lys Val Ser Asp Asn Asn Thr Phe Gln Glu Cys Ser His Tyr
                95                  100                 105

Leu Phe Ser Lys Glu Ile Thr Ser Gly Cys Gln Ile Gln Lys Glu
                110                 115                 120

Asp Ile Gln Leu Tyr Gln Thr Phe Val Val Gln Leu Gln Asp Pro
                125                 130                 135

Gln Lys Pro Gln Arg Arg Ala Val Gln Lys Leu Asn Leu Gln Asn
                140                 145                 150

Leu Val Ile Pro Arg Ala Pro Glu Asn Leu Thr Leu Ser Asn Leu
                155                 160                 165

Ser Glu Ser Gln Leu Glu Leu Arg Trp Lys Ser Arg His Ile Lys
                170                 174                 180

Glu Arg Cys Leu Gln Tyr Leu Val Gln Tyr Arg Ser Asn Arg Asp
                185                 190                 195

Arg Ser Trp Thr Glu Leu Ile Val Asn His Glu Pro Arg Phe Ser
                200                 205                 210

Leu Pro Ser Val Asp Glu Leu Lys Arg Tyr Thr Phe Arg Val Arg
                215                 220                 225

Ser Arg Tyr Asn Pro Ile Cys Gly Ser Ser Gln Gln Trp Ser Lys
                230                 235                 240

Trp Ser Gln Pro Val His Trp Gly Ser His Thr Val Glu Glu Asn
                245                 250                 255
```

-continued

```
Pro Ser Leu Phe Ala Leu Glu Ala Val Leu Ile Pro Val Gly Thr
                260                 265                 270

Met Gly Leu Ile Ile Thr Leu Ile Phe Val Tyr Cys Trp Leu Glu
                275                 280                 285

Arg Met Pro Pro Ile Pro Pro Ile Lys Asn Leu Glu Asp Leu Val
                290                 295                 300

Thr Glu Tyr Gln Gly Asn Phe Ser Ala Trp Ser Gly Val Ser Lys
                305                 310                 315

Gly Leu Thr Glu Ser Leu Gln Pro Asp Tyr Ser Glu Arg Phe Cys
                320                 325                 330

His Val Ser Glu Ile Pro Pro Lys Gly Gly Ala Leu Gly Glu Gly
                335                 340                 345

Pro Gly Gly Ser Pro Cys Ser Leu His Ser Pro Tyr Trp Pro Pro
                350                 355                 360

Pro Cys Tyr Ser Leu Lys Pro Glu Ala
                365
```